US008160708B2

(12) United States Patent
Lavie

(10) Patent No.: US 8,160,708 B2
(45) Date of Patent: Apr. 17, 2012

(54) CAPACITOR-INTEGRATED FEEDTHROUGH ASSEMBLY WITH IMPROVED GROUNDING FOR AN IMPLANTABLE MEDICAL DEVICE

(75) Inventor: Zeev Lavie, Ventura, CA (US)

(73) Assignee: Pacesetter, Inc., Sylmar, CA (US)

( * ) Notice: Subject to any disclaimer, the term of this patent is extended or adjusted under 35 U.S.C. 154(b) by 538 days.

(21) Appl. No.: 12/412,281

(22) Filed: Mar. 26, 2009

(65) Prior Publication Data

US 2009/0187229 A1    Jul. 23, 2009

Related U.S. Application Data

(63) Continuation-in-part of application No. 11/734,146, filed on Apr. 11, 2007, now Pat. No. 7,693,576.

(51) Int. Cl.
*A61N 1/372* (2006.01)

(52) U.S. Cl. ........... 607/37; 607/36; 607/38; 607/2; 439/909; 361/302

(58) Field of Classification Search ......... 607/1–3, 607/9, 17, 22, 36–38, 115–116, 112, 132; 361/302, 306.1; 600/117, 345, 333, 339, 600/344, 377, 509; 174/152 GM; 428/210, 428/496, 472, 546, 612; 623/10; 340/870.1
See application file for complete search history.

(56) References Cited

U.S. PATENT DOCUMENTS

| 5,620,476 | A | 4/1997 | Truex et al. |
| 5,650,759 | A | 7/1997 | Hittman et al. |
| 5,683,435 | A | 11/1997 | Truex et al. |
| 5,782,891 | A | 7/1998 | Hassler et al. |
| 5,817,130 | A | 10/1998 | Cox et al. |
| 5,836,992 | A | 11/1998 | Thompson et al. |
| 5,896,267 | A | 4/1999 | Hittman et al. |
| 6,414,835 | B1 | 7/2002 | Wolf et al. |
| 6,459,935 | B1 | 10/2002 | Piersma |
| 6,765,780 | B2 | 7/2004 | Brendel et al. |
| 7,012,192 | B2 | 3/2006 | Stevenson et al. |
| 7,038,900 | B2 | 5/2006 | Stevenson et al. |
| 7,110,819 | B1 | 9/2006 | O'Hara |
| 7,310,216 | B2 | 12/2007 | Stevenson et al. |
| 7,391,601 | B1 | 6/2008 | Imani |
| 7,511,938 | B2 | 3/2009 | Elam et al. |
| 7,515,964 | B1 | 4/2009 | Alexander et al. |
| 2005/0024837 | A1 | 2/2005 | Youker et al. |

(Continued)

FOREIGN PATENT DOCUMENTS

WO    2006017231 A1    2/2006

OTHER PUBLICATIONS

NonFinal Office Action, mailed Apr. 27, 2009: Parent U.S. Appl. No. 11/734,146.

(Continued)

*Primary Examiner* — Carl H Layno
*Assistant Examiner* — Paula J Stice

(57) ABSTRACT

A feedthrough assembly for use with implantable medical devices having a shield structure, the feedthrough assembly engaging with the remainder of the associated implantable medical device to form a seal with the medical device to inhibit unwanted gas, liquid, or solid exchange into or from the device. One or more feedthrough wires extend through the feedthrough assembly to facilitate transceiving of the electrical signals with one or more implantable patient leads. The feedthrough assembly is connected to a mechanical support which houses one or more filtering capacitors that are configured to filter and remove undesired frequencies from the electrical signals received via the feedthrough wires before the signals reach the electrical circuitry inside the implantable medical device.

17 Claims, 10 Drawing Sheets

U.S. PATENT DOCUMENTS

| | | |
|---|---|---|
| 2006/0009813 A1 | 1/2006 | Taylor et al. |
| 2006/0259093 A1 | 11/2006 | Stevenson et al. |
| 2007/0060970 A1 | 3/2007 | Burdon et al. |
| 2007/0255332 A1 | 11/2007 | Cabelka et al. |

OTHER PUBLICATIONS

Notice of Allowance, mailed Oct. 13, 2009: Parent U.S. Appl. No. 11/734,146.

CAPACITOR-INTEGRATED FEEDTHROUGH ASSEMBLY WITH IMPROVED GROUNDING FOR AN IMPLANTABLE MEDICAL DEVICE

CROSS REFERENCE TO RELATED APPLICATIONS

This application is a continuation-in-part of U.S. patent application Ser. No. 11/734,146, filed Apr. 11, 2007 now U.S. Pat. No. 7,693,576 entitled "CAPACITOR-INTEGRATED FEEDTHROUGH ASSEMBLY FOR AN IMPLANTABLE MEDICAL DEVICE," which is hereby incorporated by reference in its entirety.

FIELD OF THE INVENTION

The invention relates generally to implantable medical devices and more particularly to shielded feedthrough structures that connect one or more implantable patient leads to various operational circuitry within the housing of the implantable medical devices while maintaining a hermetic seal of the devices.

BACKGROUND OF THE INVENTION

A variety of implantable medical devices have been developed and employed for long-term implanted monitoring of one or more patient physiological conditions and/or delivery of indicated therapy. Implantable cardiac stimulation devices are one particular category of implantable devices which are adapted to monitor the patients' physiological conditions, including their cardiac activity, and to generate and deliver indicated therapy to treat one or more arrhythmic conditions. Implantable cardiac stimulation devices typically include either a high voltage circuit for generating high voltage waveforms, a low voltage circuit for generating relatively low voltage pacing stimuli, or both low voltage and high voltage circuits that generate waveforms for delivery to patient tissue. These devices also typically include a microprocessor-based controller which regulates the delivery of the high voltage or pacing pulse waveforms. The high and/or low voltage circuits and the controller circuitry are generally encased within a biocompatible can or housing along with a battery to power the device.

Implantable cardiac stimulation devices typically also include one or more implantable patient leads with associated electrodes. The implantable patient leads are typically connected at one end to a corresponding electrode that delivers therapy to the patient's heart and at the other end to the high and/or low voltage circuitry and controller in the can or housing. Because of the highly corrosive liquid implanted environment and because the materials and operations of the electrical circuitry are not compatible unless properly isolated from each other, the connection between the leads and the circuitry inside the housing must be such that a hermetic seal is maintained. Thus, typically, connections between the electrical circuits disposed inside the housing of the implantable device and the patient leads outside of the housing are achieved through one or more feedthrough assemblies.

The feedthrough assemblies provide for connection between the leads outside of the housing and the circuitry inside the housing while maintaining a hermetic seal. Additionally, the feedthrough assembly of an implantable medical device generally includes circuitry for filtering the electrical signals received through the patient leads so as to attenuate the spectrum of unwanted frequencies before they reach the circuitry inside the housing of the implantable device. Prior art implantable cardiac stimulation devices generally achieve this filtering through multilayer ceramic type capacitors, such as discoidal capacitors. These discoidal type capacitors are typically disposed inside the feedthrough assembly. The capacitors are very specialized, difficult to manufacture, and are therefore expensive. Because of the specialized type capacitors, prior art feedthrough assemblies occupy premium space.

As implantable medical devices are configured to be implanted inside a patient's body, their overall dimension cannot exceed certain predetermined sizes. An increase in the size of the implantable device may result in added discomfort to the patient while a decrease in size can reduce potential irritation for the patient. Further, due to the limited possible size of these devices, the amount of space inside the device is also limited. Thus, the size of various components used in an implantable medical device is an important design consideration. Smaller components may create space for additional features, while a larger component may limit the size for other features and components. The large size of the feedthrough device due to the inclusion of the filtering capacitors thus reduces the amount of space within the housing that can be used for circuitry or therapy delivering components. Hence, there is a need for a feedthrough structure that provides filtering capability but has a reduced footprint within the housing to thereby allow for more space for other components.

SUMMARY

What is described herein is a shielded feedthrough assembly for coupling implantable patient leads to electrical and other operational circuitry of an implantable medical device. In one implementation, the feedthrough assembly includes one or more feedthrough wires, an insulator, and a feedthrough case. In one embodiment, the feedthrough case is connected to a mechanical support comprised, in one specific embodiment, of multiple ceramic layers. One or more filtering capacitors are disposed inside a wire bonding ceramic substrate of the mechanical support to filter and inhibit transmission of undesired frequencies from electrical signals received through the implanted patient leads. The shielded feedthrough assembly, feedthrough wires, the mechanical support, and a housing of the implantable medical device act in combination to provide a shield between the environment and the sensitive circuitry of the device.

Thus, one embodiment includes an implantable cardiac stimulation device comprising at least one lead adapted to be implanted adjacent the patient's heart so as to delivery therapy to the patient's heart and so as to sense electrical activity indicative of the function of the patient's heart, a controller that receives signals from the at least one lead indicative of the electrical activity which is indicative of the function of the patient's heart wherein the controller also induces the delivery of therapeutic electrical stimulation to the patient's heart via the at least one lead, a casing that defines a cavity that houses the controller wherein the casing is adapted to be implanted within the body of the patient and inhibit the entry of body fluids into the cavity of the casing that contains the controller, wherein the casing defines a feedthrough opening through which the at least one feedthrough wire extends so as to be communicatively coupled to the controller, a feedthrough structure that is positioned within the feedthrough opening wherein the feedthrough structure comprises the at least one feedthrough wire which is coupled to the at least one lead, a mechanical support having a first surface that is coupled to the feedthrough structure via the first surface so as to be positioned within the casing cavity, wherein the mechanical support defines an interior volume and wherein the mechanical support defines an opening through which the at least one feedthrough wire extends so as communicatively couple the controller to the at least one lead, and at least one filter device positioned within the interior volume of the mechanical support wherein the at least one filter device is electrically coupled to the at least one feedthrough wire so as to filter unwanted signals received by the at least one feedthrough wire to inhibit transmission of the unwanted signals to the controller and wherein the at least one filter device is coupled to ground via the first surface of the mechanical support.

In one embodiment the casing of the implantable cardiac stimulation device is formed of a conductive material and the feedthrough structure defines a structure having a first and a second end that is formed of a conducting material such that when the feedthrough structure is positioned within the opening in the casing, a Faraday cage is established about the controller positioned within the cavity of the casing.

In one embodiment, the mechanical casing is multi-layer and has at least one opening that communicates with the first surface. In this embodiment, the at least one filtering device is electrically coupled to the first surface via the opening. In another embodiment, multiple layers of the mechanical casing have conductive traces.

A further embodiment includes an implantable medical device comprising at least one lead adapted to be implanted within the patient so as to provide electrical stimulation to the heart of the patient, at least one electrical sensor that senses the electrical activity of the heart of the patient and transmits electrical signals indicative of the electrical activity, a controller that induces the at least one lead to provide electrical stimulation to the heart of the patient wherein the controller receives signals from the at least one electrical sensor, a biocompatible device housing encapsulating the controller, a shield structure extending within the housing and interposed at least substantially between the at least one sensor and the controller, and a mechanical support having a first surface that is electrically coupled to ground wherein the mechanical support is mechanically coupled to the shield structure that includes at least one filtering device positioned within an opening that communicates with the first surface so as to remove undesired external frequencies from the electrical signals wherein the at least one filtering device is electrically coupled to the first surface via the opening, wherein the mechanical support is encased in a conductive material and wherein the device housing and at least portions of the shield structure together define a biocompatible seal encapsulating the controller against material exchange with an implanted environment.

Yet another embodiment includes an implantable medical device comprising one or more leads adapted to be implanted adjacent the patient's heart so as to deliver therapy to the patient's heart and so as to sense electrical activity indicative of the function of the patient's heart, a controller configured to receive electrical signals from the one or more leads indicative of the electrical activity which is indicative of the function of the patient's heart, wherein the controller comprises one or more electrical circuits, a shield structure extending within the housing and interposed at least substantially between the one or more leads and the controller, an intermediate wire termination structure that has a first surface and is coupled to the shield structure and configured to receive the one or more leads and connect each of the one or more leads to one or more of the electrical circuits, wherein the intermediate wire termination structure includes at least one filtering device positioned in the interior volume of the wire termination structure so as to remove undesired external frequencies from the electrical signals wherein the at least one filtering device is positioned within an opening in the intermediate wire termination structure that communicates with the first surface and wherein the at least one filtering device is coupled to ground via the opening and the first surface, and a biocompatible device housing encapsulating the controller and the intermediate wire termination structure.

DETAILED DESCRIPTION OF THE PREFERRED EMBODIMENT

Reference will now be made to the drawings wherein like numerals refer to like parts throughout. The following description is of the best mode presently contemplated for practicing the invention. This description is not to be taken in a limiting sense but is made merely for the purpose of describing the general principles of the invention. The scope of the invention should be ascertained with reference to the issued claims. In the description of the invention that follows, like numerals or reference designators will be used to refer to like parts or elements throughout.

Figure 1:
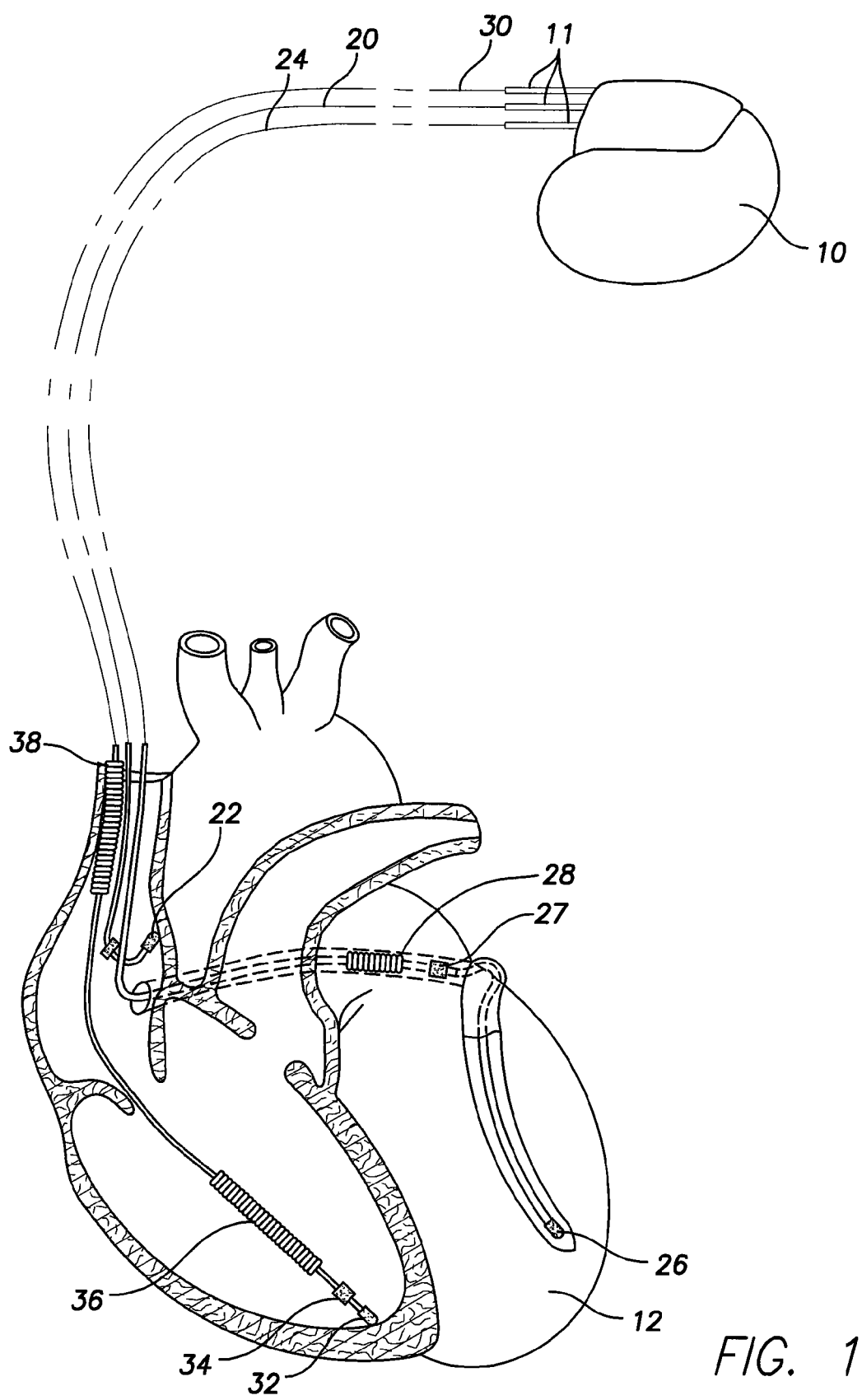
FIG. 1 is a simplified diagram illustrating an implantable stimulation device in electrical communication with at least three leads implanted into a patient's heart for delivering multi-chamber stimulation and shock therapy.

In one embodiment, as shown in FIG. 1, a device 10 comprising an implantable cardiac stimulation device 10, is in electrical communication with a patient's heart 12 by way of three leads, 20, 24 and 30, suitable for delivering multi-chamber stimulation and shock therapy. To sense atrial cardiac signals and to provide right atrial chamber stimulation therapy, the stimulation device 10 is coupled to an implantable right atrial lead 20 having at least an atrial tip electrode 22, which typically is implanted in the patient's right atrial appendage.

To sense left atrial and ventricular cardiac signals and to provide left chamber pacing therapy, the stimulation device 10 is coupled to a "coronary sinus" lead 24 designed for placement in the "coronary sinus region" via the coronary sinus ostium (OS) for positioning a distal electrode adjacent to the left ventricle and/or additional electrode(s) adjacent to the left atrium. As used herein, the phrase "coronary sinus region" refers to the vasculature of the left ventricle, including any portion of the coronary sinus, great cardiac vein, left marginal vein, left posterior ventricular vein, middle cardiac vein, and/or small cardiac vein or any other cardiac vein accessible by the coronary sinus.

Accordingly, an exemplary coronary sinus lead 24 is designed to receive atrial and ventricular cardiac signals and to deliver left ventricular pacing therapy using at least a left ventricular tip electrode 26, left atrial pacing therapy using at least a left atrial ring electrode 27, and shocking therapy using at least a left atrial coil electrode 28.

The stimulation device 10 is also shown in electrical communication with the patient's heart 12 by way of an implantable right ventricular lead 30 having, in this embodiment, a right ventricular tip electrode 32, a right ventricular ring electrode 34, a right ventricular (RV) coil electrode 36, and a superior vena cava (SVC) coil electrode 38. Typically, the right ventricular lead 30 is transvenously inserted into the heart 12 so as to place the right ventricular tip electrode 32 in the right ventricular apex so that the RV coil electrode 36 will be positioned in the right ventricle and the SVC coil electrode 38 will be positioned in the superior vena cava. Accordingly, the right ventricular lead 30 is capable of receiving cardiac signals, and delivering stimulation in the form of pacing and shock therapy to the right ventricle.

Figure 2:
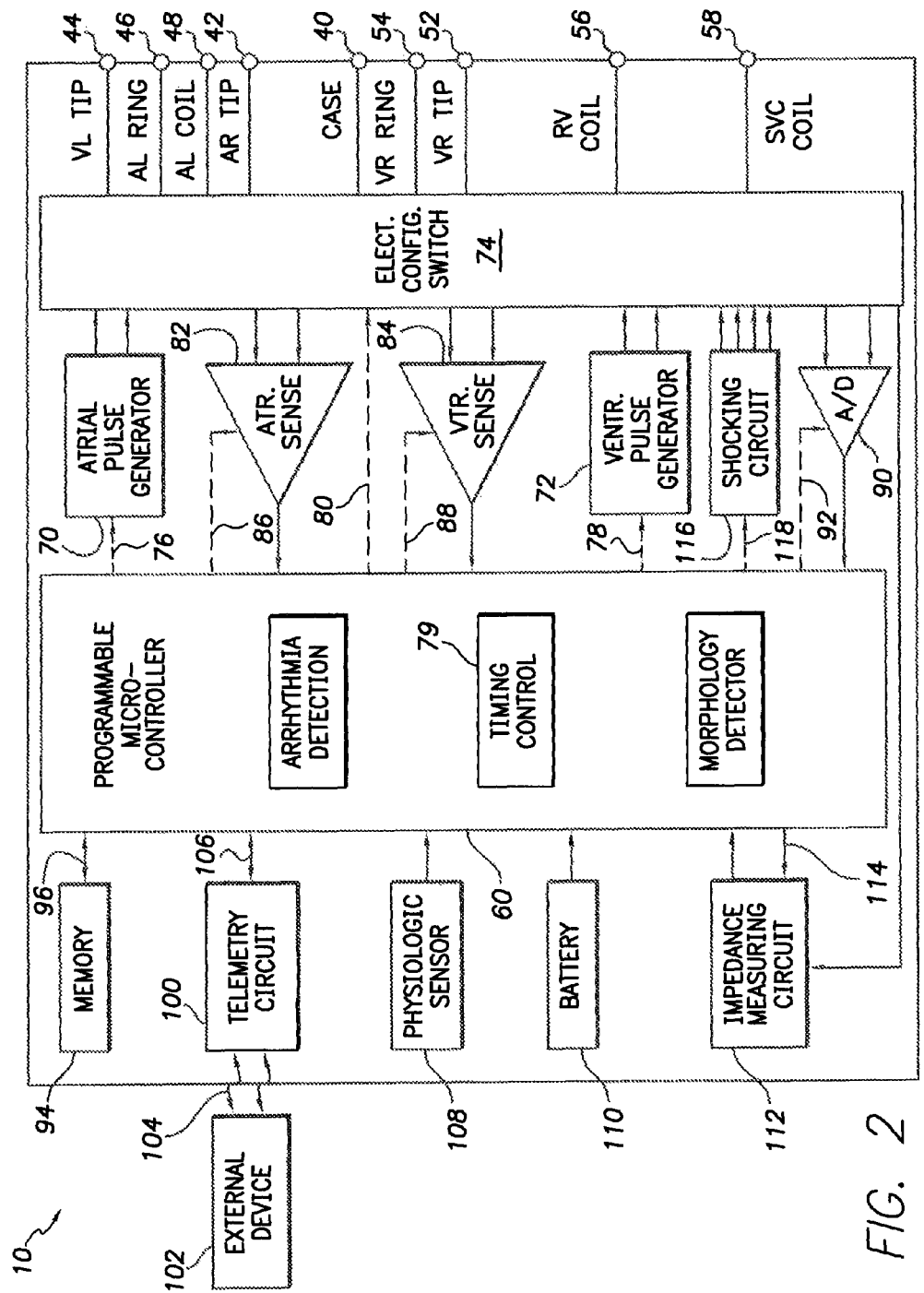
FIG. 2 is a functional block diagram of a multi-chamber implantable stimulation device illustrating the basic elements of a stimulation device which can provide cardioversion, defibrillation and pacing stimulation in four chambers of the heart.

As illustrated in FIG. 2, a simplified block diagram is shown of the multi-chamber implantable stimulation device 10, which is capable of treating both fast and slow arrhythmias with stimulation therapy, including cardioversion, defibrillation, and pacing stimulation. While a particular multi-chamber device is shown, this is for illustration purposes only and one of skill in the art could readily duplicate, eliminate or disable the appropriate circuitry in any desired combination to provide a device capable of treating the appropriate chamber(s) with cardioversion, defibrillation and pacing stimulation.

A housing 40 for the stimulation device 10, shown schematically in FIG. 2, is often referred to as the "can", "case" or "case electrode" and may be programmably selected to act as the return electrode for all "unipolar" modes. The housing 40 may further be used as a return electrode alone or in combination with one or more of the coil electrodes, 28, 36 and 38, for shocking purposes. The housing 40 further includes a connector (not shown) having a plurality of terminals, 42, 44, 46, 48, 52, 54, 56, and 58 (shown schematically and, for convenience, the names of the electrodes to which they are connected are shown next to the terminals). As such, to achieve right atrial sensing and pacing, the connector includes at least a right atrial tip terminal ($A_R$ TIP) 42 adapted for connection to the atrial tip electrode 22.

To achieve left chamber sensing, pacing and shocking, the connector includes at least a left ventricular tip terminal ($V_L$ TIP) 44, a left atrial ring terminal ($A_L$ RING) 46, and a left atrial shocking terminal ($A_L$ COIL) 48, which are adapted for connection to the left ventricular tip electrode 26, the left atrial ring electrode 27, and the left atrial coil electrode 28, respectively.

To support right chamber sensing, pacing and shocking, the connector further includes a right ventricular tip terminal ($V_R$ TIP) 52, a right ventricular ring terminal ($V_R$ RING) 54, a right ventricular shocking terminal ($R_V$ COIL) 56, and an SVC shocking terminal (SVC COIL) 58, which are adapted for connection to the right ventricular tip electrode 32, right ventricular ring electrode 34, the RV coil electrode 36, and the SVC coil electrode 38, respectively.

At the core of the stimulation device 10 is a programmable microcontroller 60 which controls the various modes of stimulation therapy. As is well known in the art, the microcontroller 60 typically includes a microprocessor, or equivalent control circuitry, designed specifically for controlling the delivery of stimulation therapy and may further include RAM or ROM memory, logic and timing circuitry, state machine circuitry, and I/O circuitry. Typically, the microcontroller 60 includes the ability to process or monitor input signals (data) as controlled by a program code stored in a designated block of memory. The details of the design and operation of the microcontroller 60 are not critical to the invention. Rather, any suitable microcontroller 60 may be used that carries out the functions described herein. The use of microprocessor-based control circuits for performing timing and data analysis functions are well known in the art.

As shown in FIG. 2, an atrial pulse generator 70 and a ventricular pulse generator 72 generate pacing stimulation pulses for delivery by the right atrial lead 20, the right ventricular lead 30, and/or the coronary sinus lead 24 via an electrode configuration switch 74. It is understood that in order to provide stimulation therapy in each of the four chambers of the heart, the atrial and ventricular pulse generators, 70 and 72, may include dedicated, independent pulse generators, multiplexed pulse generators, or shared pulse generators. The pulse generators, 70 and 72, are controlled by the microcontroller 60 via appropriate control signals, 76 and 78, respectively, to trigger or inhibit the stimulation pulses.

The microcontroller 60 further includes timing control circuitry 79 which is used to control the timing of such stimulation pulses (e.g., pacing rate, atrio-ventricular (AV) delay, atrial interconduction (A-A) delay, or ventricular interconduction (V-V) delay, etc.) as well as to keep track of the timing of refractory periods, noise detection windows, evoked response windows, alert intervals, marker channel timing, etc., which is well known in the art.

The switch 74 includes a plurality of switches for connecting the desired electrodes to the appropriate I/O circuits, thereby providing complete electrode programmability. Accordingly, the switch 74, in response to a control signal 80 from the microcontroller 60, determines the polarity of the stimulation pulses (e.g., unipolar, bipolar, combipolar, etc.) by selectively closing the appropriate combination of switches (not shown) as is known in the art. In this embodiment, the switch 74 also supports simultaneous high resolution impedance measurements, such as between the case or housing 40, the right atrial electrode 22, and right ventricular electrodes 32, 34 as described in greater detail below.

Atrial sensing circuits 82 and ventricular sensing circuits 84 may also be selectively coupled to the right atrial lead 20, coronary sinus lead 24, and the right ventricular lead 30, through the switch 74 for detecting the presence of cardiac activity in each of the four chambers of the heart. Accordingly, the atrial (ATR. SENSE) and ventricular (VTR. SENSE) sensing circuits, 82 and 84, may include dedicated sense amplifiers, multiplexed amplifiers, or shared amplifiers. The switch 74 determines the "sensing polarity" of the cardiac signal by selectively closing the appropriate switches, as is also known in the art. In this way, the clinician may program the sensing polarity independently of the stimulation polarity.

Each sensing circuit, 82 and 84, preferably employs one or more low power, precision amplifiers with programmable gain and/or automatic gain control, bandpass filtering, and a threshold detection circuit, as known in the art, to selectively sense the cardiac signal of interest. The automatic gain control enables the device 10 to deal effectively with the difficult problem of sensing the low amplitude signal characteristics of atrial or ventricular fibrillation. The outputs of the atrial and ventricular sensing circuits, 82 and 84, are connected to the microcontroller 60 which, in turn, are able to trigger or inhibit the atrial and ventricular pulse generators, 70 and 72, respectively, in a demand fashion in response to the absence or presence of cardiac activity in the appropriate chambers of the heart.

For arrhythmia detection, the device 10 utilizes the atrial and ventricular sensing circuits, 82 and 84, to sense cardiac signals to determine whether a rhythm is physiologic or pathologic. As used herein "sensing" is reserved for the noting of an electrical signal, and "detection" is the processing of these sensed signals and noting the presence of an arrhythmia. The timing intervals between sensed events (e.g., P-waves, R-waves, and depolarization signals associated with fibrillation) are then classified by the microcontroller 60 by comparing them to a predefined rate zone limit (i.e., bradycardia, normal, low rate VT, high rate VT, and fibrillation rate zones) and various other characteristics (e.g., sudden onset, stability, physiologic sensors, and morphology, etc.) in order to determine the type of remedial therapy that is needed (e.g., bradycardia pacing, anti-tachycardia pacing, cardioversion shocks or defibrillation shocks, collectively referred to as "tiered therapy").

Cardiac signals are also applied to the inputs of an analog-to-digital (A/D) data acquisition system 90. The data acquisition system 90 is configured to acquire intracardiac electrogram (IEGM) signals, convert the raw analog data into a digital signal, and store the digital signals for later processing and/or telemetric transmission to an external device 102. The data acquisition system 90 is coupled to the right atrial lead 20, the coronary sinus lead 24, and the right ventricular lead 30 through the switch 74 to sample cardiac signals across any pair of desired electrodes.

The microcontroller 60 is further coupled to a memory 94 by a suitable data/address bus 96, wherein the programmable operating parameters used by the microcontroller 60 are stored and modified, as required, in order to customize the operation of the stimulation device 10 to suit the needs of a particular patient. Such operating parameters define, for example, pacing pulse amplitude, pulse duration, electrode polarity, rate, sensitivity, automatic features, arrhythmia detection criteria, and the amplitude, waveshape and vector of each shocking pulse to be delivered to the patient's heart 12 within each respective tier of therapy.

Advantageously, the operating parameters of the implantable device 10 may be non-invasively programmed into the memory 94 through a telemetry circuit 100 in telemetric communication with the external device 102, such as a programmer, transtelephonic transceiver, or a diagnostic system analyzer. The telemetry circuit 100 is activated by the microcontroller by a control signal 106. The telemetry circuit 100 advantageously allows IEGMs and status information relating to the operation of the device 10 (as contained in the microcontroller 60 or memory 94) to be sent to the external device 102 through an established communication link 104.

In the preferred embodiment, the stimulation device 10 further includes a physiologic sensor 108, commonly referred to as a "rate-responsive" sensor because it is typically used to adjust pacing stimulation rate according to the exercise state of the patient. However, the physiological sensor 108 may further be used to detect changes in cardiac output, changes in the physiological condition of the heart, or diurnal changes in activity (e.g., detecting sleep and wake states). Accordingly, the microcontroller 60 responds by adjusting the various pacing parameters (such as rate, AV Delay, V-V Delay, etc.) at which the atrial and ventricular pulse generators, 70 and 72, generate stimulation pulses.

The stimulation device additionally includes a battery 110 which provides operating power to all of the circuits shown in FIG. 2. For the stimulation device 10, which employs shocking therapy, the battery 110 is generally capable of operating at low current drains for long periods of time and then be capable of providing high-current pulses (for capacitor charging) when the patient requires a shock pulse. The battery 110 generally also has a predictable discharge characteristic so that elective replacement time can be detected. Accordingly, embodiments of the device 10 including shocking capability preferably employ lithium/silver vanadium oxide batteries. For embodiments of the device 10 not including shocking capability, the battery 110 will preferably be lithium iodide or carbon monoflouride or a hybrid of the two.

As further shown in FIG. 2, the device 10 is shown as having an impedance measuring circuit 112 which is enabled by the microcontroller 60 via a control signal 114.

In the case where the stimulation device 10 is intended to operate as an implantable cardioverter/defibrillator (ICD) device, it generally should detect the occurrence of an arrhythmia, and automatically apply an appropriate electrical shock therapy to the heart aimed at terminating the detected arrhythmia. To this end, the microcontroller 60 further controls a shocking circuit 116 by way of a control signal 118. The shocking circuit 116 generates shocking pulses of low (up to 0.5 joules), moderate (0.5-10 joules), or high energy (11 to 40 joules), as controlled by the microcontroller 60. Such shocking pulses are applied to the patient's heart 12 through at least two shocking electrodes, and as shown in this embodiment, selected from the left atrial coil electrode 28, the RV coil electrode 36, and/or the SVC coil electrode 38. As noted above, the housing 40 may act as an active electrode in combination with the RV electrode 36, or as part of a split electrical vector using the SVC coil electrode 38 or the left atrial coil electrode 28 (i.e., using the RV electrode as a common electrode).

Cardioversion shocks are generally considered to be of low to moderate energy level (so as to minimize pain felt by the patient), and/or synchronized with an R-wave and/or pertaining to the treatment of tachycardia. Defibrillation shocks are generally of moderate to high energy level (i.e., corresponding to thresholds in the range of 5-40 joules), delivered asynchronously (since R-waves may be too disorganized), and pertaining exclusively to the treatment of fibrillation. Accordingly, the microcontroller 60 is capable of controlling the synchronous or asynchronous delivery of the shocking pulses.

Figure 3:
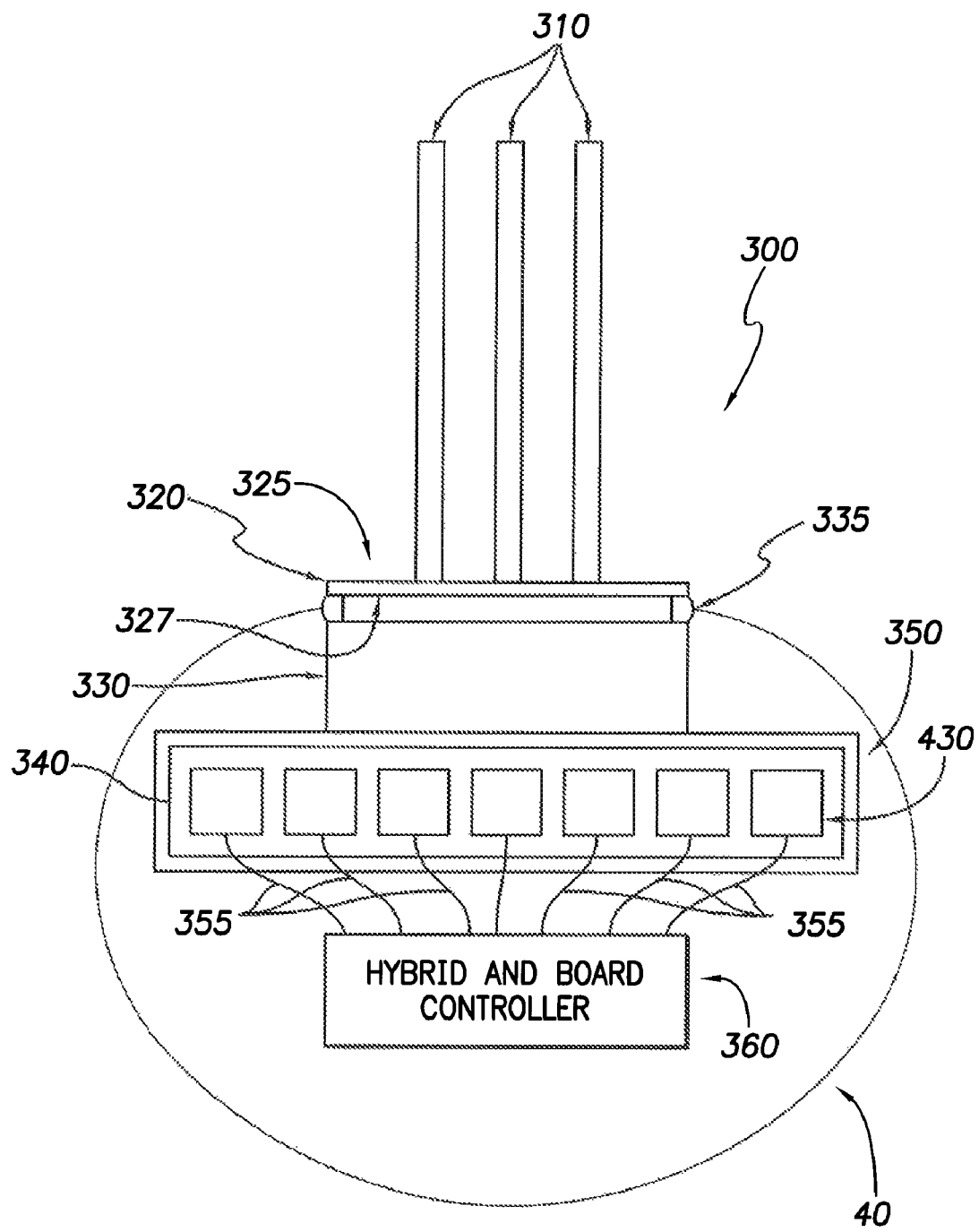
FIG. 3 illustrates a schematic frontal view of one embodiment of a shielded feedthrough assembly in an implantable medical device.

FIG. 3 illustrates a partial frontal view of one embodiment of a shielded feedthrough assembly 300 engaged to the housing of an implantable medical device, such as the device 10 of FIG. 1. The feedthrough assembly 300 is used in this embodiment to, among other things, connect one or more implantable patient leads to electrical or other operational circuitry inside the housing 40 of the implantable medical device 10.

The feedthrough assembly 300, in this particular implementation, includes three feedthrough wires 310, an insulator 320, and a feedthrough case 330. As illustrated, the feedthrough assembly 300 extends through a hermetically sealed outer wall of the housing 40 and into the housing 40 to couple one or more implantable patient leads to an electronic hybrid and controller board 360 while maintaining a hermetical seal.

The feedthrough wires 310 receive electrical signals from the patient leads and transfer the signals through the feedthrough assembly 300 to the circuitry inside the housing 40. Thus, the feedthrough wires 310 are lead wires that are each configured for connection, at an upper end, to a patient lead such as the leads 20, 24, or 30 of FIG. 1. The feedthrough wires 310 are, in one embodiment, connected to the patient leads through one or more connectors. In one configuration, the connectors are located in one or more headers such as the headers 11 shown in FIG. 1. In another embodiment, the connection between the feedthrough wires 310 and the patient leads can be achieved through welding or brazing. In yet another embodiment, the feedthrough wires 310 may form the patient leads by extending out of the feedthrough assembly and into the patient's body.

Each of the feedthrough wires 310 extend through respective openings in the insulator 320 towards the feedthrough case 330 and a mechanical support 340. Because the feedthrough wires 310 are configured to be placed in an implanted location, the feedthrough wires 310 are preferably comprised of electrically conductive biocompatible materials. In one embodiment, the feedthrough wires 310 are comprised of a platinum-iridium alloy. In other embodiments, other suitable conductive biocompatible materials such as platinum, nobium, titanium, tantalum, or combinations of these alloys can be used. In yet other embodiments, the feedthrough wires 310 may be provided with a biocompatible coating or finish.

Although, the feedthrough assembly 300 of FIG. 3 includes three feedthrough wires, it should be understood that depending on the number of implantable patient leads in a given implantable device, other embodiments may include more or less than three feedthrough wires. For example, in an embodiment where only one patient lead is implanted within the body of the patient, the feedthrough assembly includes only one feedthrough wire. Other implementations are also possible. For example, in some embodiments one feedthrough wire may be used to transfer signals from more than one patient lead. In other embodiments, the number of the feedthrough wires may exceed the number of implantable patient leads.

The feedthrough wires extend through the insulator 320. The insulator 320 is interposed between the outside environment where the device is implanted and the inside of the housing 40 of the implantable device 10. The insulator 320 has an outer surface 325 and an inner surface 327. As the outer surface 325 of the insulator 320 is, in this embodiment, exposed to the implanted environment, it is generally formed of biocompatible materials or is provided with a biocompatible coating or finish. The inner surface 327 of the insulator 320 connects the insulator 320 to the feedthrough case 330.

The feedthrough case 330 fits inside an opening (not shown) in the hermetically sealed outer wall of the housing 40 such that there is complete insulation between the outside environment and the inside of the housing 40. In one embodiment, this insulation is achieved by using a hermetic seal 335. When the feedthrough case 330 is placed inside the opening, the hermetic seal 335 is wrapped around an upper portion of the feedthrough case 330 and completely seals the inside of the housing 40 from the outside environment. A variety of other methods are also possible.

In one embodiment, the feedthrough case 330 includes three openings through which the feedthrough wires 310 extend. The feedthrough case 330 is also connected to the mechanical support 340. In one embodiment, the mechanical support 340 acts as an interface between the feedthrough wires 310 and the hybrid and controller board 360.

Generally, implantable medical devices such as, for example, the device 10 of FIG. 1, need to include a large number of connections between the various electronic circuits inside the housing 40 and one or more feedthrough wires, such as feedthrough wires 310. Because of the limited space available inside an implantable medical device, routing of the many different wires and directly connecting the different circuits to the wires has become increasingly difficult. The mechanical support 340 provides an interface through which the one or more feedthrough wires 310 can be efficiently connected to the various electronic circuits without requiring too much space. As will be discussed below, the mechanical support 340 includes an interior volume in which a plurality of traces can be formed so as to facilitate routing of electrical conductors in an efficient manner. Hence, the mechanical support 340 provides an intermediate routing component that allows for electrical conductors carrying signals to be re-routed so that the conductors occupy less volume and are better isolated from each other.

In addition to being an interface for wire connections, the mechanical support 340 can be used to house one or more circuits used for filtering the electronic signals. Generally, implantable patient leads of an implantable device are formed of materials that provide good conductivity. However, because of their high conductivity properties, these leads sometimes act as an antenna and conduct undesired electromagnetic interference signals (EMI). These undesired signals, if transmitted to the circuitry of the housing 40, can interfere with and adversely affect the normal operations of the device 10. Thus, implantable medical devices generally include filtering circuits that attenuate undesired signals before they reach the electronic circuitry of the housing 40. Previously, these filtering circuits were made of one or more discoidal type capacitors that were disposed inside the feedthrough case 330. These discoidal type capacitors are generally specialized, need to be custom built, and are thus expensive to manufacture.

In order to reduce the overall size of the feedthrough assembly, make more efficient use of the limited space of the housing, and provide a more cost-effective feedthrough assembly, in one or more embodiments of the present invention, instead of being placed inside the feedthrough case 330, the filtering capacitors are integrated into the mechanical support 340. Additionally, manufacturing costs are further reduced by using commonly-produced capacitors that are more cost-effective than discoidal type capacitors.

Figure 4A:
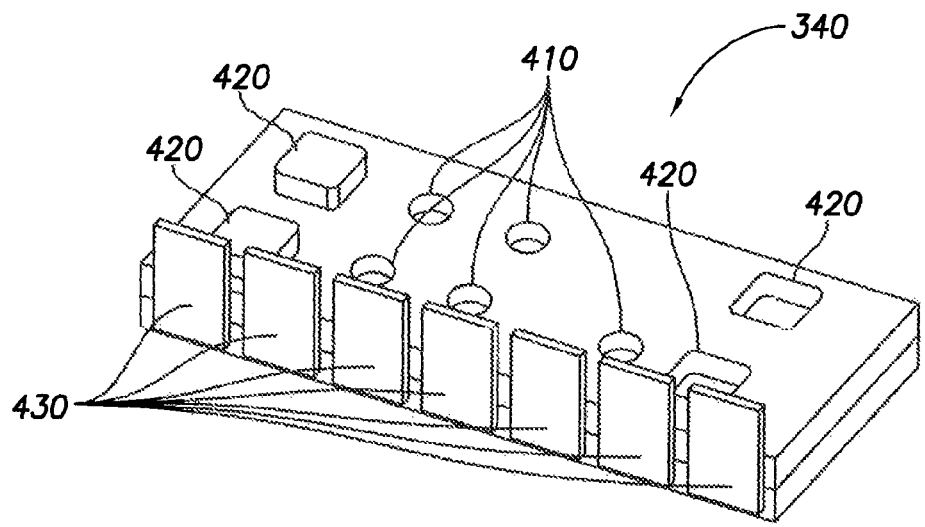
FIGS. 4A-4B are top views of one embodiment of a mechanical support in an implantable medical device.
Figure 4B:
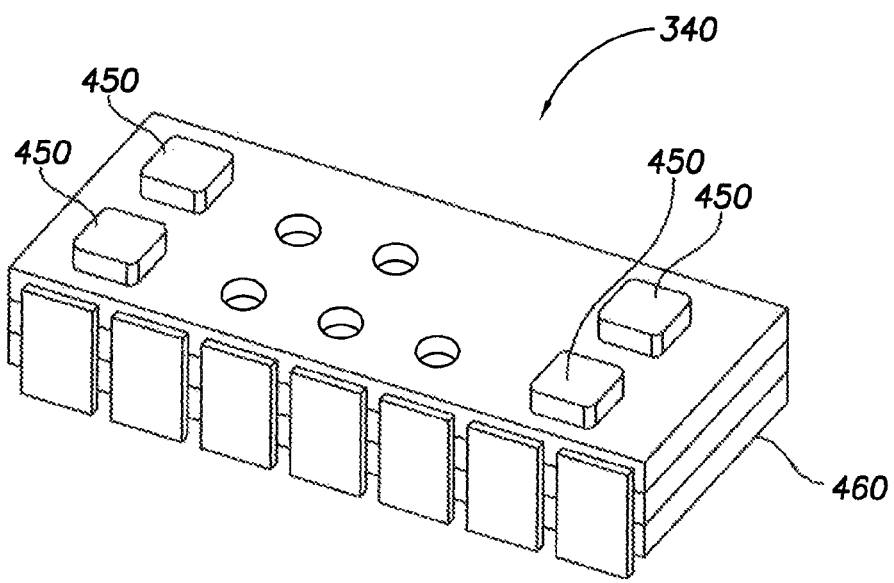
Figure 4C:
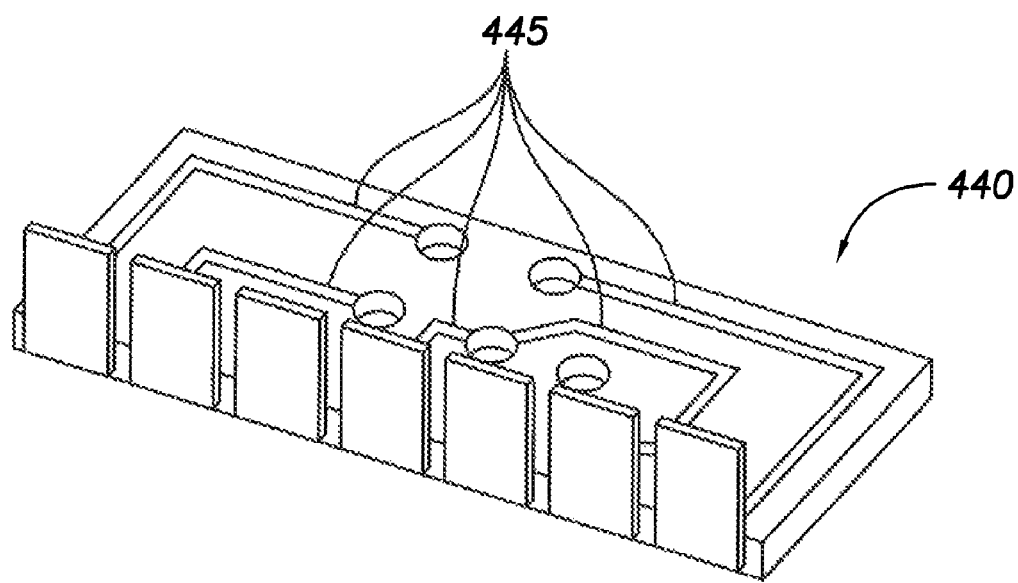
FIG. 4C is a top view of one embodiment of a ceramic layer included in the mechanical support of FIGS. 4A-4B.

FIGS. 4A-4C illustrate in more detail one embodiment of the mechanical support 340. The mechanical support 340 is a multilayer structure which includes multiple electrically insulated layers, preferably made of ceramic in one implementation, and includes one or more openings 410 through which one or more feedthrough wires, such as the feedthrough wires 310 of FIG. 3, can extend.

Additionally, the mechanical support 340 includes multiple wire-bond pads 430 that are attached to a bottom layer 460. In this embodiment, the bottom layer 460 is used with three feedthrough wires 310. In some other embodiments, the bottom layer 460 is used with four feedthrough wires in a quad polar feedthrough. In yet other embodiments, the bottom layer 460 is used with six feedthrough wires in a hex polar feedthrough. Generally, whether or not they are used, all pads 430 are wire bonded to eliminate mistakes. The wire-bond pads 430 are connected at least on one side to a bottom surface of the feedthrough case 330 of FIG. 3. In one embodiment, the wire-bond pads 430 are wire-bonded to the internal electronics of the hybrid and controller board 360. As illustrated in FIG. 3, each of the wire-bond pads 430 is connected through at least one connector 355 to the hybrid and controller board 360. Thus, the wire-bond pads 430 facilitate the transfer of signals from the feedthrough wires 310 to the electronic circuits of the housing 40.

As illustrated in FIG. 4A, one or more top layers of the mechanical support 340 also include four openings 420 configured for receiving four capacitors. As illustrated, the openings 410 extend through one or more, but not all, layers of the mechanical support 340. At lease one layer of the mechanical support 340, such as the layer 440 illustrated in FIG. 4C, includes one or more traces 445 that connect the openings 410 to the wire-bond pads 430. Thus, when capacitors 450, illustrated in FIG. 4B, are placed inside the openings 420, the traces 445 each connect one side of the capacitors 450 to one of the openings 410 and the other side of the capacitors 450 to one of the wire-bond pads 430. At least one of the wire bond pads 430 is connected to the outer surface of the feedthrough case 330 and thus acts as the system ground for the mechanical support 340. Thus in effect, the traces 445 connect the capacitors 450 between the feedthrough wires 310 and the system ground.

In one embodiment, the mechanical support 340 also includes a metal shield 350 (shown in FIG. 3) which forms the outside surface of the mechanical support 340. By encasing the mechanical support 340, the metal shield 350 creates a Faraday cage effect inside the mechanical support 340. The Faraday cage effect blocks external electrical fields and thus in effect inhibits external undesired frequencies from entering the mechanical support 340 thus shielding the conductors positioned therein. In other embodiments, the Faraday cage effect is achieved by metallization of the outer surface of the mechanical support 340.

The mechanical support 340 of FIGS. 4A-4C is a quad-polar structure. Alternative configurations of the mechanical support 340 are also possible. For example, in one embodiment, the mechanical support 340 can form a hex-polar structure. Other embodiments are also possible. For example, in one embodiment, each of the traces 445 of the mechanical support 340 is placed on a separate layer of the mechanical support 340. In another embodiment, different layers include two or more, but not all the traces 445.

A mechanical support of a feedthrough assembly is generally manufactured by stacking the various layers that form the mechanical structure on top of one another and laminating the stack with printing to form an assembly. The assembly is then fired into a final state. In implementations where the various layers are formed of ceramic, the firing generally needs to be done at a high temperature to assure proper processing.

A mechanical support 340 of an embodiment of the present invention, is manufactured, in one implementation, by stacking the one or more layers on top of one another, placing the one or more capacitors 450 into the openings 420, and encasing the mechanical support 340 into the metal shield 350 to form an assembly before firing the assembly into a final state. However, in configurations where the various layers are formed of ceramic, the various layers may be stacked on top of another and fired into a final state before connecting the capacitors to the resulting assembly. This may be done in some embodiments, because the high temperature required for firing ceramic layers may in some instances cause damage to some capacitors. Therefore, in one embodiment, the capacitors are connected to the mechanical support 340 through soldering or other similar methods known in the art, after the layers have been fired.

Figure 5:
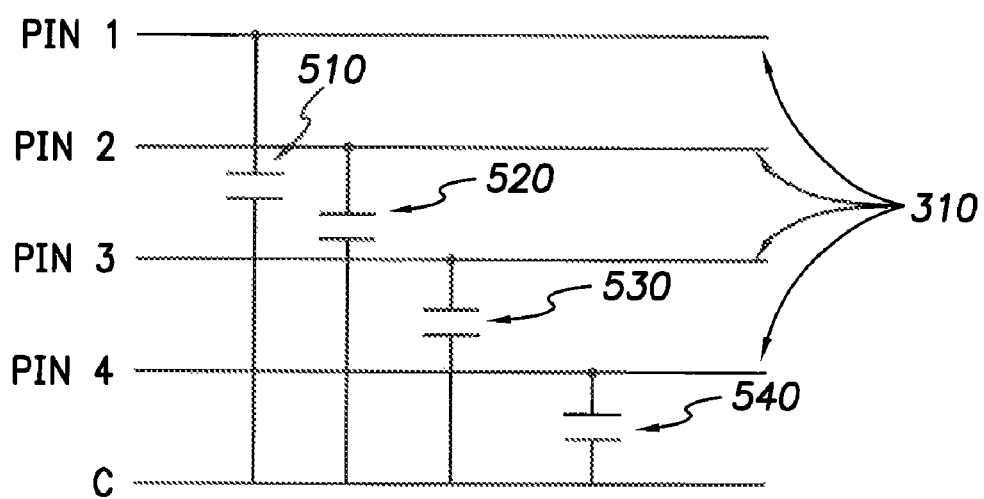
FIG. 5 is a circuit diagram of one embodiment of the filtering capacitors disposed in the mechanical support of FIGS. 4A-4B.

FIG. 5 illustrates one exemplary embodiment of a circuit diagram showing the connections between the capacitors 450 of FIG. 4B and one or more feedthrough wires 310. Each of the capacitors 510-540 of FIG. 5 illustrates one of the capacitors 450 of FIG. 4B. As illustrated, a capacitor 510 is connected between a pin 1 and the ground. Pin 1 is connected to one of the feedthrough wires 310 which is itself connected to the implantable right atrial lead 20 of FIG. 1. Because the lead 20 is itself coupled to the right atrial tip electrode 22 of FIG. 1, the capacitor 510 is thus connected to and receives signals from the right atrial tip electrode (AT) 22.

Similarly, pins 2 and 3 of FIG. 5 are connected to feedthrough wires 310 that are themselves connected to the coronary sinus lead 24 of FIG. 1. The coronary sinus lead 24 is coupled to the left atrial ring electrode (AR) 27 and the left ventricular tip electrode (VT) 26. Thus the capacitor 520 which is connected to pin 2 is connected to and receives signals from the left atrial ring electrode (AR) 27 and the capacitor 530 which is connected to pin 3 is connected to and receives signals from the left ventricular tip electrode (VT) 26.

In a similar manner, the capacitor 540 which is connected to pin 4 is connected to a feedthrough wire 310 coupled to the right ventricular lead 30 of FIG. 1. Thus, because the right ventricular lead 30 is coupled to the right ventricular ring (VR) 34 of FIG. 1, the capacitor 540 is connected to and receives signals from the right ventricular ring (VR) 34.

The capacitors 510-540 are chosen such that they can filter and remove undesired frequencies from the electrical signals they receive. Because all four capacitors are connected to the system ground, the undesired frequencies are passed directly to the system ground before they can reach the electrical circuitry of the housing 40 and result in any adverse effects.

It will be appreciated that in various embodiments the materials and processes selected can be adapted to the structural and electrical requirements as well as to the expected operating environment of the particular application. For example, as the insulator 320 and the feedthrough wires 310 are in certain embodiments not exposed to the external implanted environment, the insulator 320 and the feedthrough wires 310 can comprise materials and processes which are not generally considered biocompatible, such as solder and/or certain conductive materials.

Figure 6A:
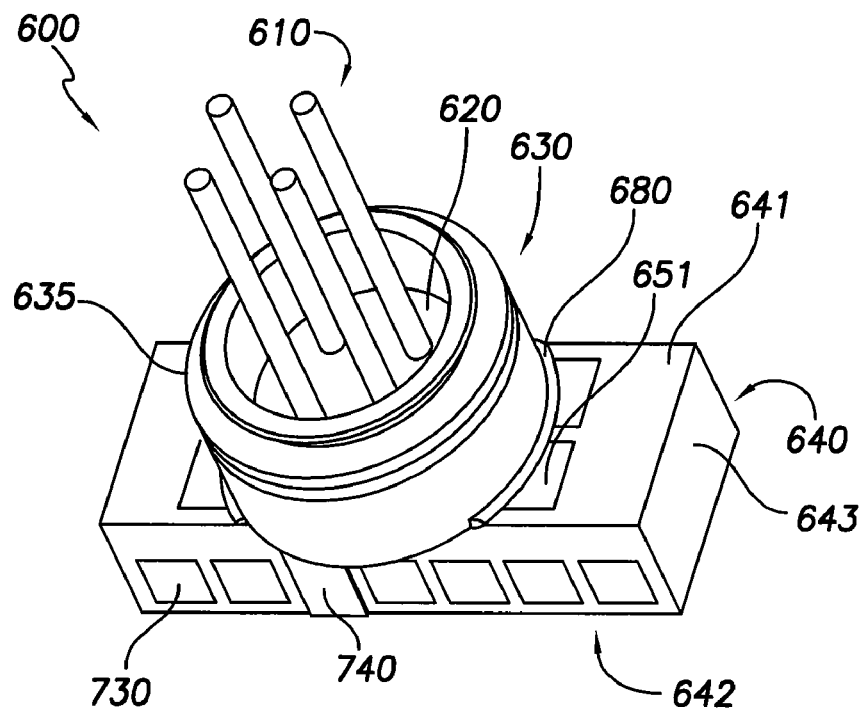
FIGS. 6A and 6B are top and bottom perspective views illustrating a second embodiment of a feedthrough assembly.
Figure 6B:
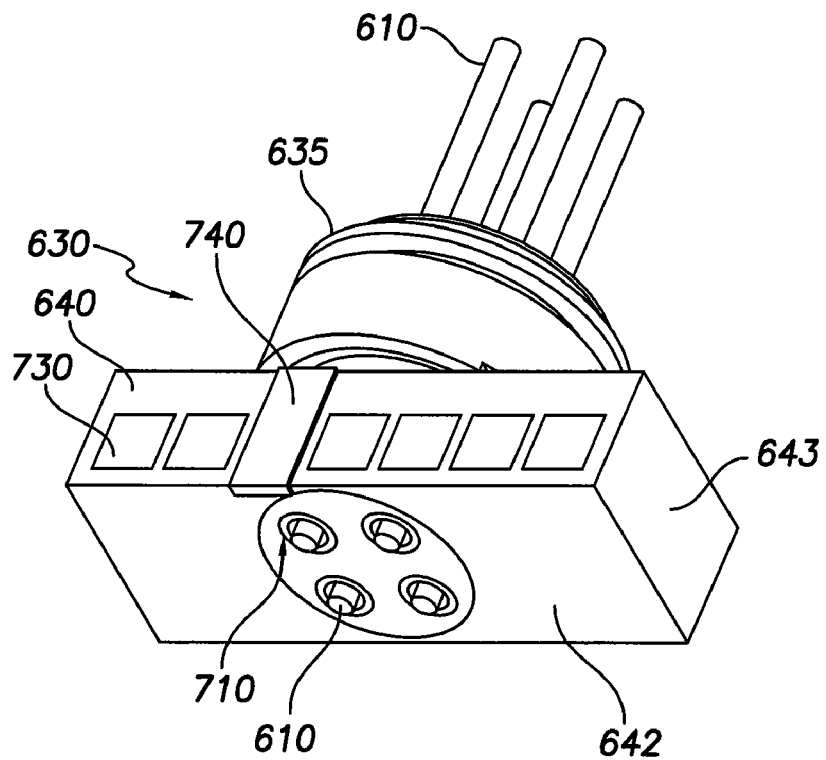

FIGS. 6A and 6B illustrate an alternative embodiment of a feedthrough assembly 600 similar to the assembly 300 described above. In this implementation, a mechanical support 640 has been modified to provide for a more efficient use of the interior space of the mechanical support 640. As shown in FIGS. 6A and 6B, the assembly 600 includes feedthrough wires 610 that can be coupled to the leads 22, 24, 30 in the same manner as described above. The feedthrough wires enter into a feedthrough case 630 that is substantially similar to the case 330 described above and includes an insulator 620 and a hermetic seal 635 that engages with the housing 40 in the same manner as described above.

The case 630 is mounted on an upper surface 641 of a mechanical support 640 of the present embodiment. The upper surface 641 of the mechanical support 640 include openings 651 that receive capacitors 750 in a similar manner as described above. The mechanical support 640 further includes openings 710 that receive the feedthroughs 610 in the same manner as the openings 410 described above in conjunction with FIGS. 4A-C. In this implementation, the configuration of the interior space of the mechanical support 640 has been re-oriented so as to increase the amount of space that can be used for positioning the capacitors 750 so that the capacitors 750 are positioned more closely to the feedthroughs 610 to thereby reduced parasitic inductances.

The mechanical support further includes wire bonding pads 730 that allow for wire bond connections via connectors 355 to a hybrid and board controller 360 in substantially the same manner as described in conjunction with FIG. 3 above. As shown in FIGS. 6A and 6B, however, a conductive ground connection 740 extends from the upper surface 641 of the mechanical support to a lower surface 642. In this implementation, both the upper surface 641 and the lower surface 642 of the mechanical support 640 are coated with a conductive coating. In one implementation, the upper surface 641 and the lower surface 642 are plated with an electrolytic nickel and gold using a well-known process. The conductive ground connection 740 thereby provides a uniform ground connection between the surfaces 641 and 642. Further the side surfaces, other than the surface having the wire bonding pads 730 may also be coated for shielding purposes in the manner described above.

In the embodiment discussed above in connection with FIGS. 3 and 4, the capacitors 420 are connected to ground via traces 445 formed in a layer within the mechanical support 340. In some circumstances, this can result in the loss of volume for the connection of the capacitors to the feedthrough which can result in the feedthrough being separated from the capacitors 750. This greater spacing can result in an increase in the parasitic capacitances and inductances which can affect the transmission of signals into the interior of the housing 40 which can potentially affect the overall operation of the device.

Figure 7A:
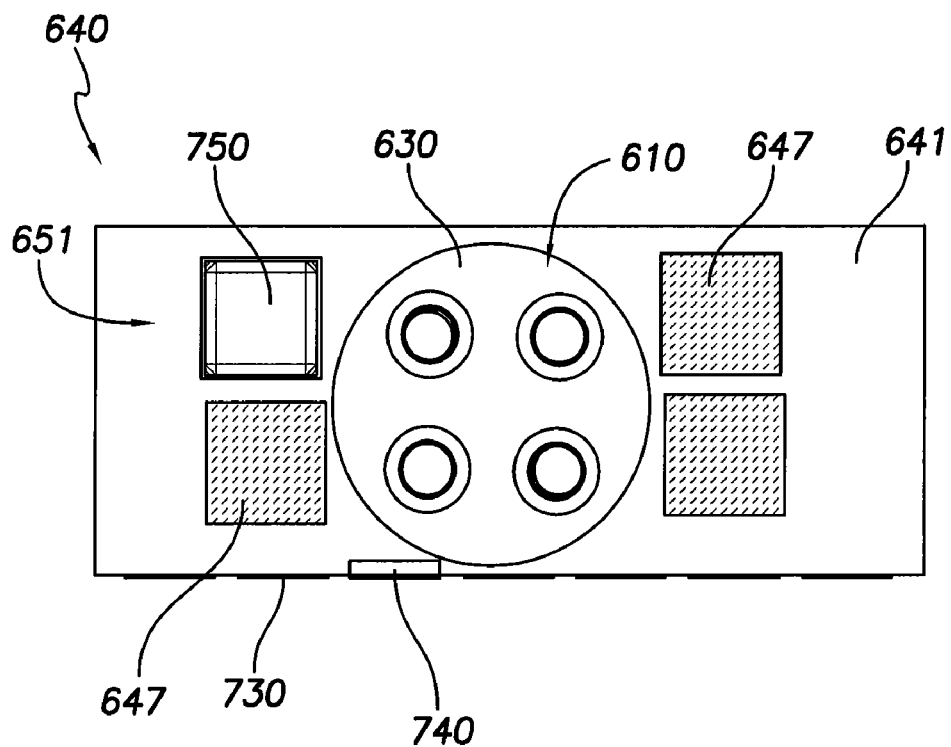
FIGS. 7A-7C are side cross-sectional, top cross-sectional and detailed side-cross sectional views of the support member of the second embodiment of the feedthrough assembly of FIGS. 6A and 6B illustrating how the capacitors of the support member can be grounded via a surface.
Figure 7B:
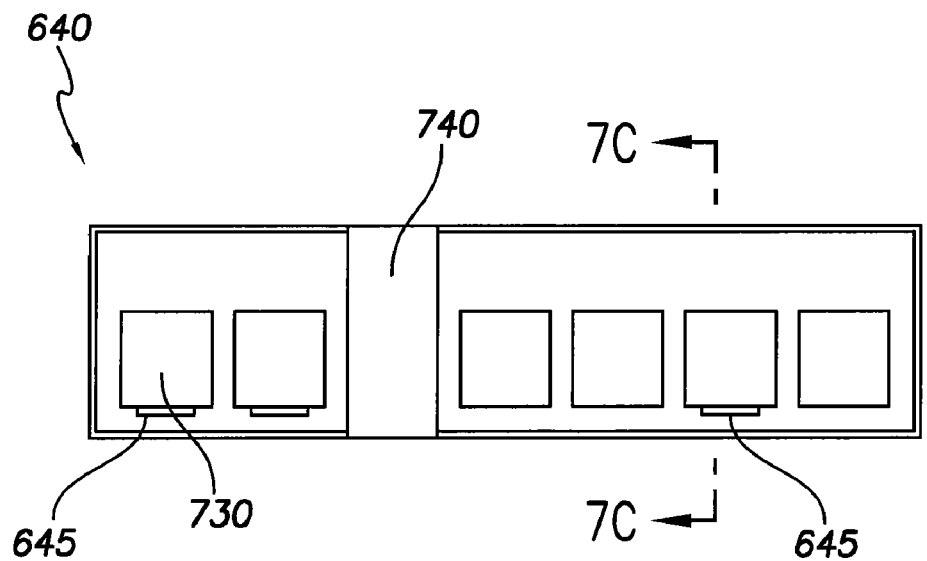
Figure 7C:
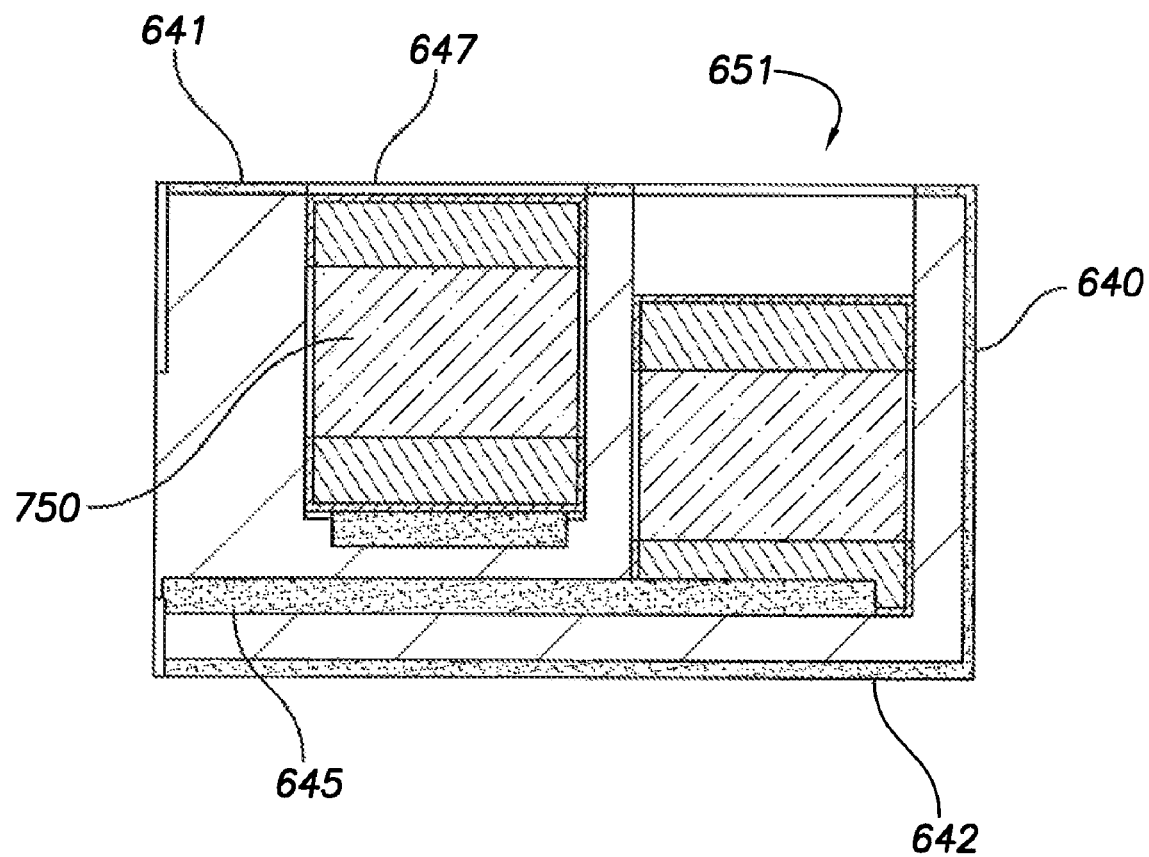
Figure 8A:
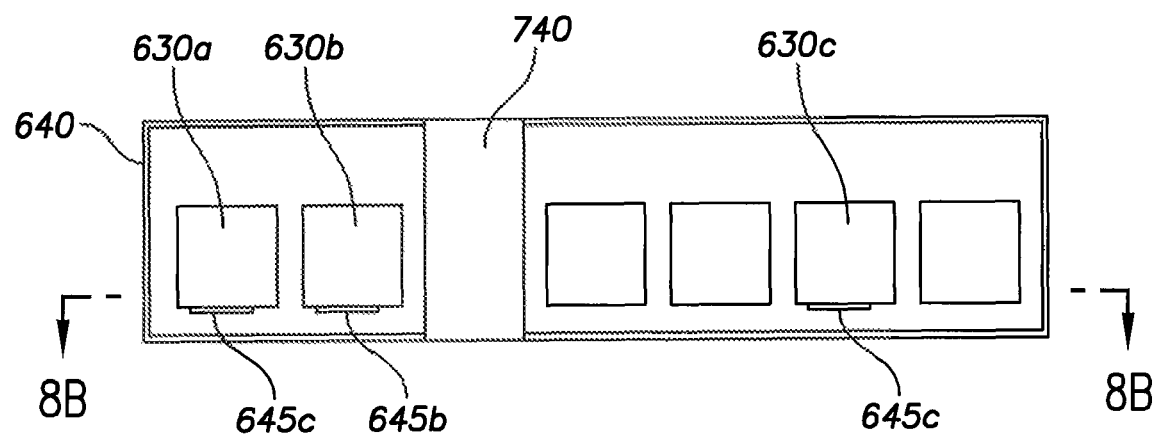
FIGS. 8A-8D are side and top cross sectional views of the support member of FIGS. 6A and 6B taken at two different levels illustrating how the capacitors and feedthroughs can be interconnected at different levels.
Figure 8B:
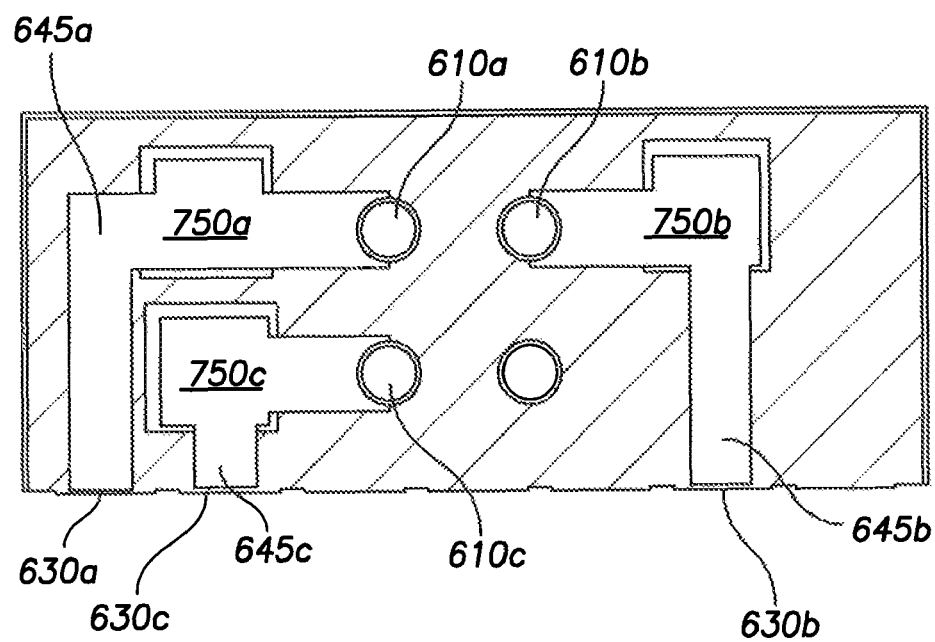
Figure 8C:
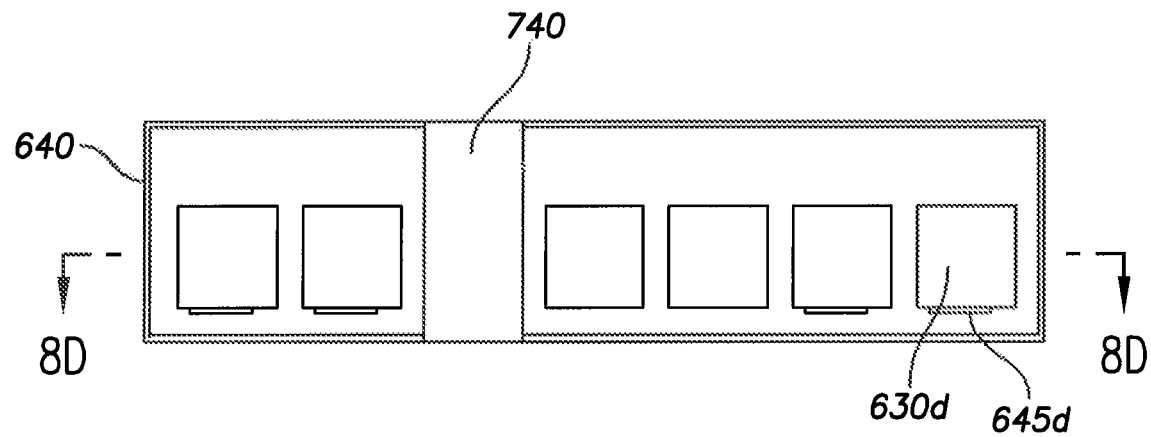
Figure 8D:
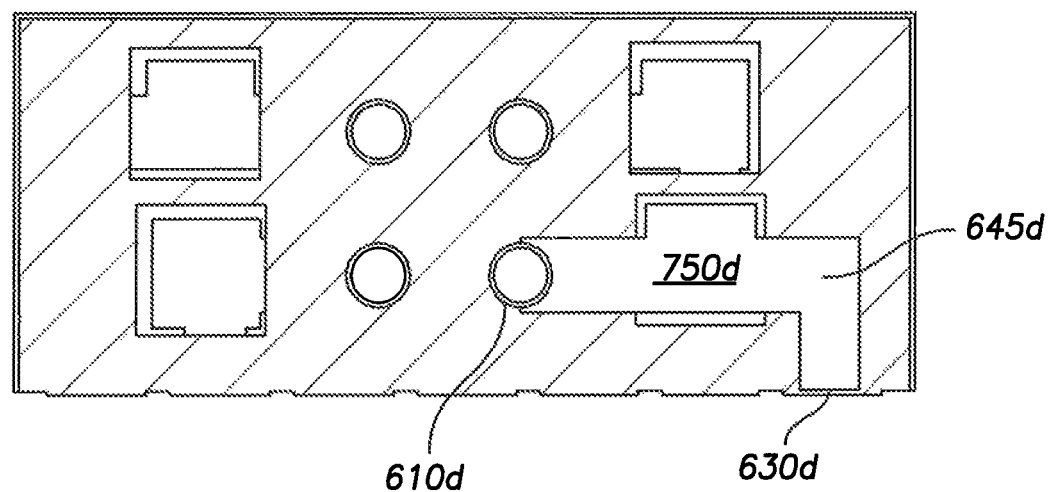

To address this issue, the embodiment of FIGS. 6-8 connects the capacitors 750 to ground via the conductive upper surface 641 of the mechanical support 640. More specifically, referring to FIGS. 7A-7C, the capacitors 750 are positioned within the openings 651. One end of the capacitors 750 are connected to the feedthroughs 610 via traces 645 in the same manner as discussed above so as to achieve a grounding circuit similar to that shown in FIG. 5. As shown in FIG. 7C, the traces 645 are located proximate the bottom surface 642 of the mechanical support 640 on one or more levels as will be discussed in greater detail hereinbelow.

The openings 651 are exposed to the upper surface 641 of the mechanical support 640 and a conductive material 647, such as conductive polymer, is used to fill the openings up to the level of the surface 641 to thereby electrically interconnect the capacitors 750 to the surface 641. In this way, all of the capacitors 750 can be coupled to the upper surface 641 of the mechanical support 340 and then subsequently be coupled to ground, in a manner that will be described hereinbelow, without requiring a layer of traces to be formed within the interior of the mechanical support 640. The electrical connection between the capacitors 750 and the surface 641 can be accomplished in any of a number of ways including the use of conductive epoxy, solder and the like.

Referring back to FIG. 6A, the feedthrough case 630 is preferably made of a conductive material such as titanium and can be electrically coupled to the upper surface 641 of the mechanical support 640 as a result of physical contact. As is also illustrated in FIG. 6A, a conductive polymer bead 680 or like structure may also be positioned about the outer circumference of the feedthrough case 630 wherein the feedthrough case 630 is positioned proximate the upper surface 641 to thereby enhance the electrical interconnection. As discussed above in connection with the embodiment of FIGS. 3 and 4, the feedthrough case 630 is electrically coupled to the housing 40 which serves as ground.

Thus, by coating the upper surface 641 with a conductive material and electrically connecting the capacitors 750 to the upper surface 641 via solder or conductive polymer, the capacitors 750 can be coupled to ground via the feedthrough case 630 without requiring the use of a layer of wiring traces within the mechanical support 640. This increases the amount of available space to form the traces to connect the capacitors 750 to the feedthroughs 610 thereby improving the function of the device as described above.

As is also illustrated in FIGS. 7A-7C and 8A-8D, the interconnection of the feedthrough 610 to the wire bond pads 730 may be formed on a plurality of different levels within the mechanical support 640. More specifically, in the exemplary embodiment shown in FIGS. 8A and 8B, three of the feedthroughs 610a-610c may be connected to capacitors 750a-750c and corresponding wire bond pads 730a-730c via traces 645a-645c on one vertical level B-B of the mechanical support 640. Further, a higher level C-C shown in FIGS. 8C and 8D may be used to connect a fourth feedthrough 610d to a capacitor 750d and a wire bond pad 730d via a trace 645d. By offsetting the traces 645 in a vertical direction, the feedthroughs 610 can be positioned more closely to the wire bonds 730 which can further reduce parasitic capacitances and inductances and thereby improve the performance of the device.

Thus, various embodiments of the present invention provide the capability to incorporate signal filtering into implantable medical device applications. Various embodiments provide and maintain an effective hermetic seal such that possible harmful contaminants are inhibited from entry to or exit from an implantable medical device which might otherwise interfere with intended operation of the device, and/or cause injury to the patient. Various embodiments also shield or inhibit interference between various electronic modules of an implantable medical device. The various embodiments facilitate reducing the size and the cost of a feedthrough assembly used in implantable medical devices.

Although the above disclosed embodiments of the present teachings have shown, described and pointed out the fundamental novel features of the invention as applied to the above-disclosed embodiments, it should be understood that various omissions, substitutions, and changes in the form of the detail of the devices, systems and/or methods illustrated may be made by those skilled in the art without departing from the scope of the present teachings. Consequently, the scope of the invention should not be limited to the foregoing description but should be defined by the appended claims.

What is claimed is:

1. An implantable cardiac stimulation device comprising:
   at least one lead adapted to be implanted adjacent the patient's heart so as to delivery therapy to the patient's heart and so as to sense electrical activity indicative of the function of the patient's heart;
   a controller that receives signals from the at least one lead indicative of the electrical activity which is indicative of the function of the patient's heart wherein the controller also induces the delivery of therapeutic electrical stimulation to the patient's heart via the at least one lead;
   a casing that defines a cavity that houses the controller wherein the casing is adapted to be implanted within the body of the patient and inhibit the entry of body fluids into the cavity of the casing that contains the controller, wherein the casing defines a feedthrough opening through which the at least one feedthrough wire extends so as to be communicatively coupled to the controller and wherein the casing defines a ground for the implantable cardiac stimulation device;
   a feedthrough structure that is positioned within the feedthrough opening wherein the feedthrough structure comprises the at least one feedthrough wire which is coupled to the at least one lead;

a mechanical support having a first surface that is coupled to the feedthrough structure via the first surface so as to be positioned within the casing cavity, wherein the mechanical support defines an interior volume and wherein the mechanical support defines an opening through which the at least one feedthrough wire extends so as communicatively couple the controller to the at least one lead; and at least one filter device positioned within the interior volume of the mechanical support wherein the at least one filtering device is electrically coupled to the at least one feedthrough wire so as to filter unwanted signals received by the at least one feedthrough wire to inhibit transmission of the unwanted signals to the controller and wherein the at least one filter device is coupled to ground via the first surface of the mechanical support.

2. The device of claim 1, wherein the casing is formed of a conductive material and the feedthrough structure defines a structure having a first and a second end that is formed of a conducting material such that when the feedthrough structure is positioned within the opening in the casing, a Faraday cage is established about the controller positioned within the cavity of the casing.

3. The device of claim 1, wherein the mechanical support is formed of a multi-layer ceramic material having openings and traces within the interior volume so as to allow electrical interconnection between the at least one filtering device and the at least one feedthrough wire.

4. The device of claim 3, wherein the multi-layer ceramic material comprises at least one opening though which the at least one filtering device extends wherein the opening communicates with the first surface.

5. The device of claim 4, wherein the first surface is conductive and a conductive material is positioned within the opening so as to extend from the at least one filtering device and the conductive first surface.

6. The device of claim 5, wherein the feedthrough structure is also conductive and is positioned on the first surface so as to be conductively linked to the at least one filtering device.

7. The device of claim 6, wherein the feedthrough structure is conductively coupled with the case.

8. The device of claim 6, wherein the feedthrough structure is further coupled to the first surface via a conductive solder.

9. The device of claim 3, wherein the mechanical support is comprised of a top, a middle, and a bottom ceramic layer.

10. The device of claim 9, wherein the top and the middle ceramic layers comprise at least one opening though which the at least one filtering device extends.

11. The device of claim 9, wherein traces are disposed on the bottom ceramic layer.

12. The device of claim 11, wherein traces are disposed on a plurality of ceramic layers.

13. The device of claim 3, wherein the at least one filter device comprises at least one capacitor that is adapted for filtering undesired EMI frequencies.

14. The device of claim 13, wherein the mechanical support comprises four capacitors which are electrically coupled to at least one wire bond pad.

15. The device of claim 1, wherein the mechanical support is encased in a conductive material, such that a Faraday cage is established about the mechanical support.

16. The device of claim 1, wherein the at least one lead comprises a pacing lead adapted to provide low voltage pacing pulses to the heart.

17. The device of claim 1, wherein the at least one lead comprises a high voltage lead adapted to provide high voltage cardioversion or defibrillation waveforms to the patient's heart.

* * * * *